United States Patent [19]

Szarvasi

[11] 3,973,033

[45] Aug. 3, 1976

[54] COMPOSITIONS AND METHODS FOR PRODUCING A VASODILATORY EFFECT WITH A NAPHTHYL TETRAHYDROFURFURYL AMINO-ESTER

[75] Inventor: Etienne Szarvasi, Charbonnieres-les-Bains, France

[73] Assignee: Lipha Lyonnaise Industrielle Pharmaceutique, Lyon, France

[22] Filed: Sept. 26, 1973

[21] Appl. No.: 400,918

Related U.S. Application Data

[62] Division of Ser. No. 275,638, July 27, 1972, Pat. No. 3,872,112.

[30] Foreign Application Priority Data

July 29, 1971  France .............................. 71.27823

[52] U.S. Cl. ................................................. 424/285
[51] Int. Cl.² ........................................... A61K 31/34
[58] Field of Search .................................... 424/285

[56] References Cited
UNITED STATES PATENTS 3,334,096  8/1967  Szarvasi ......................... 424/285 X
3,445,574  3/1967  Szarvasi ......................... 424/285 X Primary Examiner—James O. Thomas, Jr.
Assistant Examiner—Daren M. Stephens
Attorney, Agent, or Firm—Browdy and Neimark

[57] ABSTRACT

The present invention relates to substituted tetrahydrofurfuryl aminoesters. The novel tetrahydrofurfuryl dialkyl aminoesters are represented by the formula

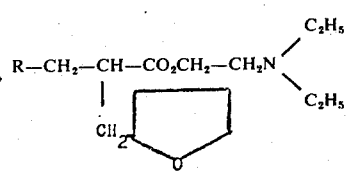

in which R is a member of the group formed by the 2-naphthyl, 2-naphthyl substituted in the 6-position with alkoxy and 5,6,7,8-tetrahydro-1-naphthyl radicals. The addition salts with the therapeutically acceptable acids, the starting and intermediate products of these aminoesters, also form the subject of the invention.

The novel aminoesters and their salts, endowed with peripheral and cerebral vasodilatory properties, are of particular interest in human therapeutics.

7 Claims, No Drawings

COMPOSITIONS AND METHODS FOR PRODUCING A VASODILATORY EFFECT WITH A NAPHTHYL TETRAYDROFURFURYL AMINO-ESTER

This is a division of application Ser. No. 275,638, filed July 27, 1972, now U.S. Pat. No. 3,872,112.

The present invention relates to substituted tetrahydrofurfuryl aminoesters, the processes for the preparation thereof and their applications. It is also concerned with obtaining initial products and intermediate products in the synthesis of these novel aminoesters.

A certain number of aminoesters derived from 3-(1-naphthyl) 2-(2-tetrahydrofurfuryl)-propionic acid are known which are endowed with vasodilatory and antispasmodic properties, particularly in the U.S. Pat. No. 3,455,574 patented on the 20$^{th}$ March 1969 and U.S. Pat. No. 3,334,096 patented on the 1$^{st}$ August 1967, both in the name of Etienne Szarvasi.

These different dialkylaminoesters and particularly the acid oxalate of 2-diethylaminoethyl-3-(1-naphthyl)-(2-tetrahydrofurfuryl)-propionate, sold under the mark "Praxilene", contain a 1-naphthyl nucleus in their molecule.

It has been found in accordance with the present invention that the substitution in the 1-position by the naphthalenic nucleus is not essential and that the saturation of one of the nuclei of the naphthyl radical permits the biological activity to be preserved.

The novel tetrahydrofurfuryl dialkylaminoesters according to the invention have a double activity as peripheral vasodilators and cerebral vasodilators without a hypotensive effect and they are represented by the formula:

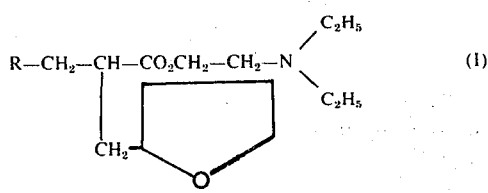

in which R is a member of the group formed by the 2-naphthyl radical, the 2-naphthyl radical substituted with alkoxy such as methoxy in the 6-position and 5,6,7,8-tetrahydro-1-naphthyl radical.

It has been discovered that the substitution in the 6-position of the naphthalene nucleus by an alkoxy radical, particularly a methoxy radical, has a favorable influence on the therapeutic activity, while a substitution in the 4-position can correspond to compounds which can be considered as practically inactive, such as the case of 2-N-diethylaminoethyl-3-(4-chloro-1-naphthyl)-2-(2'-tetrahydrofurfuryl)-propionate.

The derivatives of these compounds, which also form the subject of the invention, are their addition salts with the acids acceptable for therapeutic uses.

The novel compounds can be obtained according to the invention by condensation of a carboxylic acid of formula:

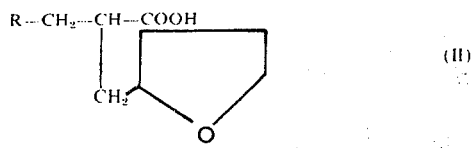

in which R has the same meaning as previously, with an amino derivative of formula:

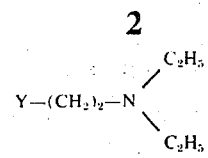

in which Y is a halogen, in the presence of an alkali agent. According to one method of procedure, the condensation is carried out under heat in the presence of an alkaline mineral agent, such as potassium carbonate, in an alcoholic solvent medium, such as isopropanol.

For preparing the acid oxalates of the compounds of formula I, the aminoesters as previously obtained are salified with oxalic acid in acetone medium.

The disubstituted carboxylic represented by the formula II, in which R is the possibly alkoxy substituted 2-naphthyl radical, are obtained by saponification and decarboxylation by an alkali in the presence of an alcohol, preferably benzyl alcohol, alkyl malonates of formula:

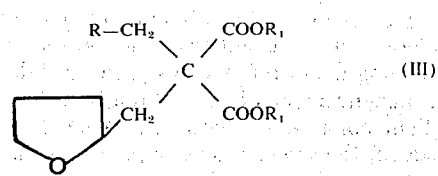

in which R has the same meaning as before and R$_1$ is a lower alkyl radical, the said malonates being themselves prepared by reacting a sodium alcoholate with ethyl-(2-tetrahydrofurfuryl)-malonate and then condensing the sodium derivative obtained with the halide of formula R—CH$_2$Y, in which Y represents a halogen.

The disubstituted carboxylic acids of formula II and the disubstituted ethyl malonates of formula:

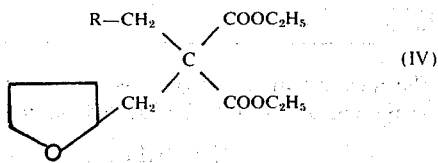

in which R has the same meaning as previously, which are capable of being used particularly as intermediate products in the preparation of the aminoesters of formula I, are novel and for this reason form part of the invention.

A process or preparation has also been found, with which it is possible to obtain 1-chloromethyl-5,6,7,8-tetrahydronaphthalene in a pure state, free from its isomer, which is a starting product in the preparation of:

ethyl-α-/5,6,7,8-tetrahydro-1-naphthylmethyl/α-(2-tetrahydrofurfuryl)-malonate.

The 1-chloromethyl-5,6,7,8,-tetrahydronaphthalene in pure form and as such a new industrial product is obtained by reacting (5,6,7,8-tetrahydro-1-naphthyl)-methanol with thionyl chloride in the presence of pyridine and in a chlorinated organic solvent medium. The product, obtained by distillation with a purity of 86 %, is recrystallized in hexane, yielding the chlorinated derivative with a purtiy of 100 %, by vapour phase chromatography.

Examples illustrating the invention in non-limiting manner are given below

EXAMPLE 1

Ethyl-α-(2-naphthylmethyl)-(2-tetrahydrofurfuryl)-malonate

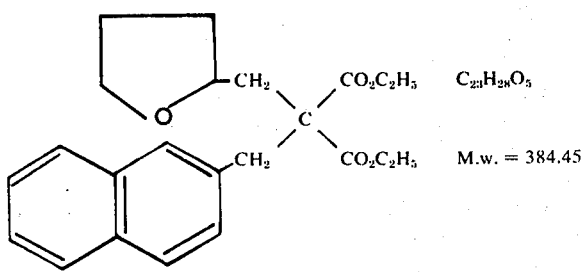

$C_{23}H_{28}O_5$

M.w. = 384.45

4.5 (mol/12) of sodium methylate and 50 ml of ethyl carbonate are placed in a reactor. 19.5 g (mol/12.5) of ethyl-(2-tetrahydrofurfuryl)-malonate are added thereto. A gently exothermal reaction is produced, with development of a yellow colouring. Heating under reflux takes place for 30 minutes and the solution becomes brown. After cooling, 15 g (mol/11.7) of 2-chloromethyl naphthalene are introduced dropwise. Heating under reflux takes place for 8 hours; with the commencement of the heating, the formation of sodium chloride is confirmed. After cooling, water is added, the organic layer is poured off and dried over anhydrous sodium sulphate.

Distillation of the organic layer permits 18.2 g of a viscous yellow liquid to be isolated, the said liquid having a boiling point b.p.$_{0.8}$ = 200°C, with a yield of 55.5 % (theoretical yield 32.8 g).

Vapour phase chromatography (XE 60 − T = 265°), single peak.

| Gravimetric analysis | C % | H % |
|---|---|---|
| Calculated | 71.83 | 7.33 |
| Found | 71.81 | 7.35 |

The infrared spectrum obtained can be superimposed on the spectrum of its 1-naphthyl isomer.

EXAMPLE 2

3-(2-Naphthyl)-2-(2-tetrahydrofurfuryl)-propionic acid

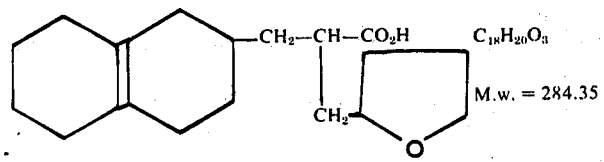

$C_{18}H_{20}O_3$

M.w. = 284.35

57 g (mol/6.75) of ethyl α(2-naphthylmethyl)-α-(2-tetrahydrofurfuryl)-malonate, 20 g of 85 % KOH (17 g = (mol/3.3) are heated under reflux for 8 hours in 300 ml of benzyl alcohol. The benzyl alcohol is driven off under vacuum. The crude potassium salt is dissolved in water. The aqueous solution is washed with benzene and acidified. An oil precipatates. It is dissolved in the boiling mixture of 100 ml of hexane + 30 ml of ethyl acetate. After cooling, there are obtained in two lots: 25.6 g of white crystals, of melting point F = 85°-90°c with a yield of 61 % (theoretical yield: 42 g).

| Acidity Index | Calculated | 197 |
|---|---|---|
|  | Found | 193 |

The product is used as such in the sequence of operations, but for the analytical specimen, it is purified by changing to its methyl ester $C_{19}H_{22}O_3$, M.w. = 298.37, prepared as follows: the following are heated under reflux for 6 hours: 31 g (mol/9.15) of the above acid in 140 ml of methanol and 7 ml of concentrated $H_2SO_4$. The usual treatment yields 21.9 g of a yellow liquid of boiling point b.p.$_{0.5}$ = 175°-178°C with a yield of 67.5 % (theoretical yield: 32.5 g). VPC XE 60 (T = 260°): single peak - infrared spectrum conforms. The above ester, when saponified, yields the corresponding acid. For this purpose, there are heated under reflux for 5 hours: 21.3 g (mol/13.9) of the above ester, 50 ml of ethyl alcohol and 5 g (4.26 g = (mol/13.1) of 85 % KOH. After evaporating the alcohol, the oily, crude potassium salt is dissolved in water. The aqueous solution is washed with ether. Acidification is carried out with hydrochloric acid. An oily precipitate is obtained, which becomes solid and crystalline, when it is taken up in ether. After filtering with suction and washing with diisopropyl ether, there is obtained a first lot of 5.9 g of white product with a melting point of 97°-99°C and a second lot of 7.3 g of white product, m.p. = 60°-65°C. The yield is 13.2 g, i.e. 64.5 % (theoretical yield: 20.5 g).

The first lot, after recrystallisation from hexane and diisopropyl ether (1:1) melts at 104°-105°C. White crystals.

A.I. Calculated 197
Found 196
I.R. : CO at 1740 cm $^{-1}$

| Gravimetric analysis | C % | H % |
|---|---|---|
| Calculated | 76.04 | 7.09 |
| Found | 76.00 | 7.07 |

The acid seems to exist in two forms: threo and erythro. The second lot probably represents a mixture. The first lot alone was prepared for the analysis.
Potassium salt: m.p. = 238°-240°C.

EXAMPLE 3

Ethyl-2-diethylamino-3-(2-naphthyl)-2-(2-tetrahydrofurfuryl)-propionate

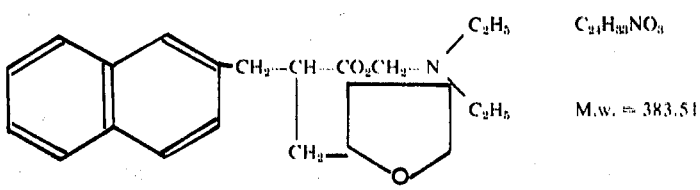

$C_{24}H_{33}NO_3$

M.w. = 383.51

14.6 g (mol/9.45) of potassium carbonate are placed in 130 ml of isopropanol and there are added there to 15 g (mol/11.45) of 2-chlorethyl diethylamine hydrochloride, followed by the solution of 25 g (mol/11.38) of 3-(2-naphthyl)-(2-tetrahydrofurfuryl)propionic acid in 40 ml of tepid isopropanol. Heating under reflux takes place for 8 hours. After evaporation to dryness, the residue is taken up in water made acid with hydrochloric acid, washed with ether and the aqueous layer is made alkaline with sodium hydroxide and then extracted with ether. By distillation, there are obtained 14 g of a light yellow liquid of boiling point b.p.$_{0.6}$ = 195°–200°C, with a yield of 41.6 % (theoretical yield: 33.6 g).

With the second distillation, the boiling point is b.p.$_{0.6}$ = 204°–206°C.

| Gravimetric Analysis | C % | H % | N % |
|---|---|---|---|
| Calculated | 75.18 | 8.67 | 3.65 |
| Found | 75.20 | 8.65 | 3.68 |

1740 cm$^{-1}$ : CO ester
1500 cm$^{-1}$ :
1600 cm$^{-1}$ : aromatic vibration
3050 cm$^{-1}$ : benzenic CH
Acid oxalate : $C_{26}H_{35}NO_7$ - M.w. = 473.55.

11.3 g (mol/34) of the above base are dissolved in 15 ml of acetone. This solution is introduced dropwise into a solution of 3.7 g (mol/34) of twice-hydrated oxalic acid in 22 ml of acetone. 10 g of white crystals are obtained, m.p. = 70°–85°C. After recrystallisation (ethyl acetate), the yield is 8.8 g = 63.5 %. (theoretical yield: 13.9 g). M.p. = 68°–70°C. Following a fresh recrystallisation (ethyl acetate), the product becomes deliquescent on filtering with suction and it is solidified after one night in air. White crystals. M.p. = 80°–82°C.
A.I. Calculated 236
    Found 234
The mother liquors, to which ether is added, yield a second lot, of which the melting point is 90°–92°C.

| Gravimetric analysis | C % | H % | N % |
|---|---|---|---|
| Calculated | 65.95 | 7.45 | 2.95 |
| Found | 65.91 | 7.47 | 3.00 |

The infrared spectrum of the first lot can be practically superimposed on its isomer, 1-naphthyl, known under the commercial mark of Praxiline.

| Gravimetric analysis (first lot) | C % | H % | N % |
|---|---|---|---|
| Calculated | 65.95 | 7.45 | 2.95 |
| Found | 65.95 | 7.48 | 2.94 |

EXAMPLE 4

1-Chloromethyl-5,6,7,8-tetrahydronaphthalene

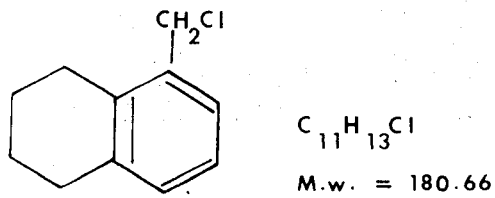

$C_{11}H_{13}Cl$

M.w. = 180.66

61 g (0.376 mol) of (5,6,7,8-tetrahydro-1-naphthyl)-methanol with a purity of 78 % are dissolved in 450 ml of chloroform, in the presence of 35 g (0.38 mol) of pyridine. 90 ml of thionyl chloride in solution in 30 ml of chloroform are introduced dropwise and between 30 and 40°C into the solution which is obtained and this is heated under reflux for 6 hours. After partial evaporation of the chloroform and the thionyl chloride excess, washing is carried out with water and with a sodium bicarbonate solution, followed by drying over anhydrous sodium sulphate. Distillation of the oily residue permits the isolation of a liquid of boiling point b.p.$_{0.5}$ = 81°–83°C, with a purity of 86 % (vapour phase chromatography), and this is taken up in 150 ml of hot hexane. The crystallisation is seeded by scratching with a glass rod. There are isolated 29.5 g of a product melting at 51°–52°C, with a yield of 56 % (theoretical yield = 53 g, depending on the degree of purity of the starting product). Vapour phase chromatography confirms a purity of 100 %.

| Gravimetric analysis | C % | H % | Cl % |
|---|---|---|---|
| Calculated | 73.12 | 7.25 | 19.62 |
| Found | 73.10 | 7.25 | 19.65 |

Nuclear magnetic resonance
    Carbon tetrachloride solvent
    Internal reference tetramethylsilane
    3 aromatic protons at 6.9–7.1 ppm
    2 benzyl protons at 4.5 ppm
    2 groups of 4 protons, each at 1.7–2 ppm
        $CH_2$ of the tetraline
        2.6–3 ppm
    Total = 13 protons.

EXAMPLE 5

Ethyl -α-/
5,6,7,8-tetrahydro-1-naphthylmethyl/-α-(2-tetrahydrofurfuryl)-malonate

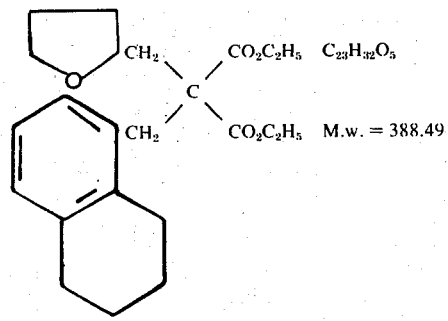

$C_{23}H_{32}O_5$

M.w. = 388.49

12.5 g (0.232 mol) of sodium methylate are suspended in 150 ml of distilled ethyl carbonate. 55 (0.226 mol) of ethyl-2-tetrahydrofurfuryl)-malonate are introduced. Heating under reflux takes place for one hour. At the temperature of 70°C, there are added 41 g (0.228 mol) of 1-chloromethyl-5,6,7,8-tetrahydronaphthalene in 120 ml of ethyl carbonate, followed by heating under reflux for 8 hours. Water is added in the cold, followed by dilute hydrochloric acid (pH = 7). The organic layer is dried and distilled.

I 59 g b.p.$_{0.6}$ = 180°–181°C
II 3 g b.p.$_{0.6}$ = 181°–185°C

Vapour phase chromatography = fractions I and II identical and pure at 100 %. The analytical sample, twice distilled, has a boiling point b.p.$_{0.5}$ = 183°–184°C.
Yield = 62 g = 70 % (theoretical yield = 88.5 g).

| Gravimetric analysis | C % | H % |
|---|---|---|
| Calculated | 71.11 | 8.30 |
| Found | 71.15 | 8.33 |

Infrared : CO at 1740 cm$^{-1}$

EXAMPLE 6

3-(5,6,7,8-tetrahydro-1-naphthyl)-2-(2-tetrahydrofurfuryl)-propionic acid

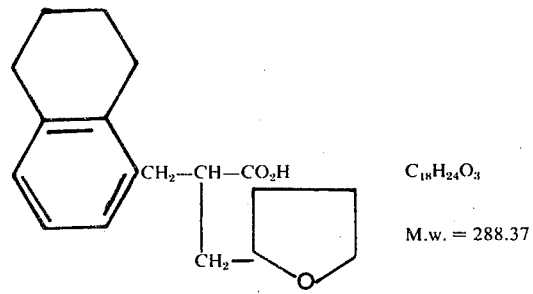

$C_{18}H_{24}O_3$

M.w. = 288.37

62 g (0.159 mol) of ethyl$\alpha$-(5,6,7,8-tetrahydro-1-naphthylmethyl)-$\alpha$-(2-tetrahydrofurfuryl) malonate, 22 g 0.39 mol of 85 % KOH and 320 ml of benzyl alcohol are heated under reflux for 8 hours. The solution is evaporated to dryness under vacuum and the semi-solid residue is dissolved in the minimum quantity of water (200 ml) and the aqueous layer is washed with hexane. After drying the solution and evaporation to dryness, there are obtained 27 g of distillable oil, b.p.$_{0.7}$ = 205°–207°C.
A.I. Calculated 194
 Found 184
Infrared, CO badly resolved at 1710 and 1740 cm$^{-1}$
Yield = 27 g = 58.5 % (theoretical yield = 46 g).

The distillate, left for a few days at ambient temperature, starts to crystallise. 50 ml of hexane and 10 ml of ethyl acetate are added thereto. White crystals are separated out, m.p. = 88°–90°C.

After recrystallisation (ethyl acetate-hexane), the constants are as follows:
M.p. = 90°–93°C
A.I. Calculated 194
 Found 188
Infrared : CO at 1700 cm$^{-1}$

| Gravimetric analysis | C % | H % |
|---|---|---|
| Calculated | 74.96 | 8.38 |
| Found | 74.98 | 8.35 |

Subsequently, the crude acid, not crystallised, is used as such. It is also possible to obtain the crystalline form of the acid from the crude, undistilled oil, by adding a mixture of hexane and ethyl acetate.

EXAMPLE 7

N-2-diethylaminoethyl-3-(5,6,7,8-tetrahydro-1-naphthyl)-2-(2-tetrahydrofurfuryl)-propionate

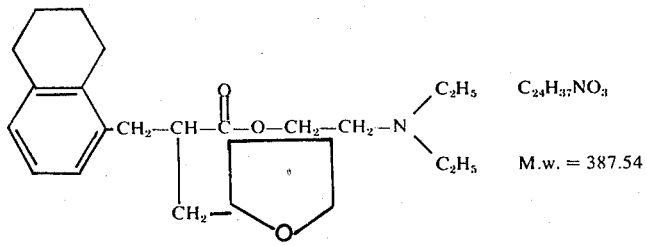

$C_{24}H_{37}NO_3$

M.w. = 387.54

8.1 g (0.058 mol) of potassium carbonate are suspended in 135 ml of isopropanol and there are added thereto 13 g (0.096 mol) of N-diethylamino-2-chlorethane and a solution of 27 g (0.094 mol) of crude acid from the preceding example, in solution in 45 ml of hot isopropanol. The mixture is heated under reflux for 9 hours. It is evaporated to dryness and the residue is treated with acidified water. It is washed with ether, treated again in basic medium and extracted with ether.
Distillation
20 g of light yellow oil, b.p.$_{0.7}$ = 193°–195°C. Yield = 20 g = 55 % (Theoretical yield = 36.4 g).
Vapour phase chromatography : purity = 100 %, however, the analytical sample is twice distilled, b.p.$_{0.4}$ = 175°–177°C.

| Gravimetric analysis | C % | H % | N % |
|---|---|---|---|
| Calculated | 74.39 | 9.62 | 3.61 |
| Found | 74.36 | 9.58 | 3.63 |

Infrared : CO at 1740 cm$^{-1}$ Acid oxalate : $C_{26}H_{39}NO_7$ : M.w. = 477.57.

7.74 g (0.02 mol) of the above ester are dissolved in 10 ml of acetone. This solution is introduced dropwise into a solution of of 2.52 g (0.02 mol) of dihydrated oxalic acid in 10 ml of acetone. A few drops of ether are added until cloudiness is formed. It is left in the refrigerator and then suction-filtered. 8.8 g of a white product, m.p. = 82°–84°C, are separated with a yield of 93 % (theoretical yield = 9.5 g). When recrystallised once in a mixture of diisopropyl ether and acetone, the melting point remains unchanged.
A.I. Calculated 234
 Found 234

| Gravimetric analysis | C % | H % | N % |
|---|---|---|---|
| Calculated | 65.39 | 8.23 | 2.93 |
| Found | 65.35 | 8.23 | 3.00 |
| Infrared : wide band at | 3600 to 3400 cm$^{-1}$ OH | | |
| | 1700 to 1720 cm$^{-1}$ CO. | | |

EXAMPLE 8

Ethyl-α-/6-methoxy-2-naphthylmethyl/-α-/2-tetrahydrofurfuryl/-malonate

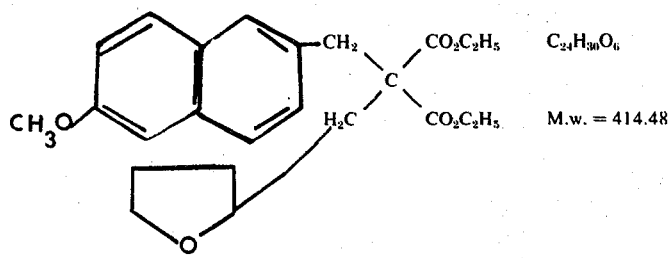

11 g (0.22 mol) of sodium methylate are suspended in 100 ml of ethyl carbonate and 46.5 g (0.191 mol) of ethyl-(2-tetrahydrofurfuryl)-malonate are introduced thereinto. The exothermic reaction causes the temperature to rise to 40°C. Following this reaction, heating under reflux takes place for 1 hour and then there are introduced 40 g (0.194 mol) of 6-methoxy-2-chloromethylnaphthalene, in solution in 140 ml of ethyl carbonate. Heating under reflux takes place for 1 hour and then there are introduced 40 g (0.194 mol) of 6-methoxy-2-chloromethylnaphthalene, In solution in 140 ml of ethyl carbonate. Heating under reflux takes place for 16 hours and the sodium chloride which forms is dissolved by adding water. The decanted organic layer is re-washed with water. After drying and evaporating the solvent, an oily residue is obtained which is taken up in a mixture of 500 ml of water and 125 ml of alcohol. After cooling, the yellow crystals are suction-filtered. Yield: 61.4 g = 77.5 % (theoretical yield: 79 g). M.p. = 60°–61°C (softening at 57°C).

The product can be used as such. For the analysis, it is recrystallised from hexane: M.p. = 63°–65°C (white). The crude oil can be distilled: b.p. 1.2 to 1.3 millibars = 229°–231°C.

Gravimetric analysis

|  | C % | H % |
|---|---|---|
| Calculated | 69.55 | 7.29 |
| Found | 69.58 | 7.30 |

Infrared spectrum
CO at 1730 and 1740 cm$^{-1}$.

13.2 g (0.2 mol) of 85 % potash, 200 ml of benzyl alcohol and 41.4 g (0.1 mol) of malonate from Example 1 are heated under reflux for 8 hours. After heating for 45 minutes, a copious deposit of potassium salt is already formed. The benzyl alcohol is evaporated under vacuum. The remaining potassium salt is dissolved in water. The aqueous solution is washed with benzene and then with ether. It is acidified with hydrochloric acid. Copious release of carbon dioxde gas. After scratching, the product crystallises. It is purifed, by extracting it with ether. After drying the organic layer and evaporation to dryness the oily residue is caused to crystallise in 100 ml of boiling diisopropyl ether. Yield: 20 g = 64 % (theoretical yield 31.4 g). M.p. = 100°–107°C.

Recrystallisation

From 2 g of product in 20 ml of hexane and 70 ml of diisopropyl ether, there are obtained 1.3 g of m.p. = 115°–116°C. After a second recrystallisation, the melting point is 117°–119°C.

| Acidity index | |
|---|---|
| Calculated | 178 |
| Found | 174 |

Infrared spectrum
CO at 1720 cm$^{-1}$.

Gravimetric analysis

|  | C % | H % |
|---|---|---|
| Calculated | 72.60 | 7.05 |
| Found | 72.56 | 7.08 |

EXAMPLE 10

N-2-Diethylaminoethyl-3-(6-methoxy-2-naphthyl)-b 2-(2-tetrahydrofurfuryl)-propionate

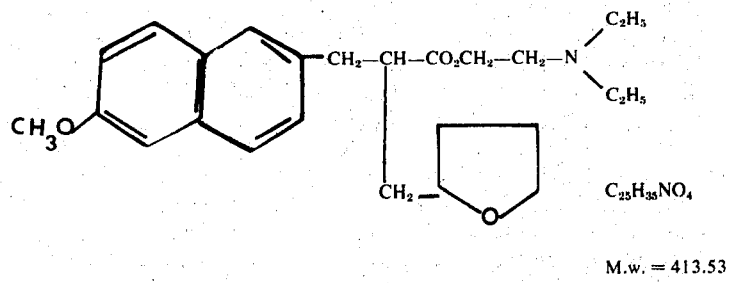

EXAMPLE 9

3-(6-Methoxy-2-naphthyl)-2-(2-tetrahydrofurfuryl)-propionic acid

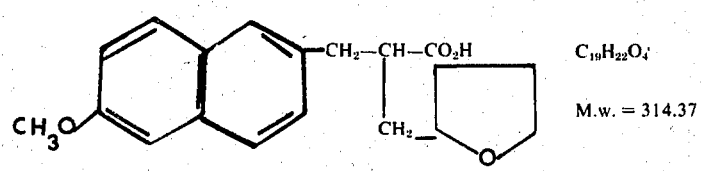

18 g (0.0575 mol) of the acid of Example 9 are dissolved in 80 ml of isopropanol, and there are added thereto 5 g (0.036 mol) of dry K$_2$CO$_3$, followed by a solution of 8 g (0.059 mol) of 2-N-diethylamino chloroethane in 30 ml of isopropanol. Heating under reflux takes place for 10 hours, whereafter the solvent is evaporated and the residue is taken up in dilute HCl. The acid solution is washed with benzene and introduced into alkali medium and extracted with ether. Distillation yields 10.5 g of an oil, of which the boiling point is 230°–235°C at 1.36 millibars. Yield: 10.5 g = 44 % (theoretical yield = 23.8 g).

With the second distillation:
b.p. = 235°–237°C at 1.22–1.36 millibars.

| Infrared spectrum | | | |
|---|---|---|---|
| CO at 1730 cm⁻¹. | | | |
| Gravimetric analysis | C % | H % | N % |
| Calculated | 72.61 | 8.53 | 3.38 |
| Found | 72.64 | 8.56 | 3.37 |
| Acid oxalate | | | |
| $C_{27}H_{37}NO_8$  m.w. = 503.56. | | | |

4.1 g (0.01 mol of the above base, in 10 ml of acetone, are added to 1.3 g (0.01 mol) of dihydrated oxalic acid in 10 ml of acetone. After being left in the refrigerator and suctionfiltered, the yield is 5 g = quantitative. M.p. = 102°–104°C. After recrystallisation (ethyl acetate and hexane), the melting point is 102°–103°C.

| Acidity index | | | |
|---|---|---|---|
| Calculated | 223 | | |
| Found | 220 | | |
| Gravimetric analysis | C % | H % | N % |
| Calculated | 64.40 | 7.40 | 2.78 |
| Found | 64.42 | 7.38 | 2.77 |

Infrared spectrum

Can be superimposed on that of the acid oxalate of 2-diethylaminoethyl-3-(1-naphthyl)-2-(tetrahydrofurfuryl)-propionate, marketed under the mark Praxiline.

PHARMACOLOGICAL TESTS

The peripheral vasodilatory activity was studied by femoral rotametry on the dog.

The control product is the acid oxalate of 2-diethylaminoethyl-3-(1-naphthyl)-2-tetrahydrofurfuryl-propionate, marketed under the mark Praxiline. The activity coefficient is arbitrarily fixed at 100.

The activity of the acid oxalate of 2-diethylaminoethyl-3-(2-naphthyl)-2-(2-tetrahydrofurfuryl)-propionate (first lot of Example 3) is at least equal to that of the Praxilene. The Lethal Dose₅₀ (per os mouse) is equal to 1040 mg/kg. The activity coefficient of the acid oxalate of 2-N-diethylaminoethyl of 3-(5,6,7,8-tetrahydro-1-naphthyl)-2-(2-tetrahydrofurfuryl)-propionate in femoral rotametry is equal to 100. The $LD_{50}$ (per os mouse) is equal to 1350 mg/kg. The activity of the acid oxalate of 2-N-diethylaminoethyl-3-(6-methoxy-2-naphthyl)-2-(2-tetrahydrofurfuryl)-propionate in femoral rotametry is 96 %. The $LH_{50}$ (per os mouse) is equal to 2000 mg/kg.

The new active principles present a vasodilatory action at cerebral level. It was proved with the dog by measuring the blood flow of two vertebral arteries by means of a Shipley-Wilson ratameter.

The comparison with papaverine administered under the same conditions discloses an activity which is three to four times better with the compounds of the invention and which is not accompanied by hypotension, as in the case of papaverine.

The daily dose sufficient for obtaining the desired therapeutic result on human beings varies from about 150 to 300 mg/kg.

It is easy to administer the compounds of the invention: the pharmaceutical doses can be formulated in the usual manner with the aid of conventional excipients and adjuvants in the form of tablets, gelatine capsules, injectable solutions, etc...

What I claim is:

1. A medicine particularly useful as a peripheral and cerebral vasodilator comprising a pharmaceutically acceptable excipient and, as active principle, a cerebral vasodilatory-effective amount of a tetrahydrofurfuryl aminoester of the formula:

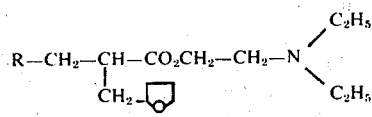

in which R is a member of the group consisting of the 2-naphthyl radical, the 6-alkoxy-2-naphthyl radical, and the 5, 6, 7, 8-tetrahydro-1-naphthyl radical.

2. A medicine in accordance with claim 1 wherein the active principle is an addition salt with a therapeutically acceptable acid of the tetrahydrofurfuryl aminoester defined in claim 1.

3. A medicine in accordance with claim 1 wherein the active principle is ethyl-2-diethylamino-3-(2-naphthyl)-2-(2-tetrahydrofurfuryl)-propionate or an addition salt thereof with therapeutically acceptable acid.

4. A medicine in accordance with claim 1, wherein the active principle is N-2-diethylaminoethyl-3(3,6,7,8-tetrahydro-1 naphthyl)-2-(2-tetrahydrofurfuryl) propionate or an addition salt thereof with therapeutically acceptable acid.

5. A medicine in accordance with claim 1 wherein the active principle is N-2-diethylaminoethyl-3-(6 methoxy-2 naphthyl) -2-(2-tetrahydrofurfuryl)-propionate or an addition salt with therapeutically acceptable acid.

6. A method of producing a vasodilatory effect in a patient in need of said therapy comprising:
administering, in unit dosage form, to a patient in need of said therapy, a vasodilatory-effective nontoxic amount of a tetrahydrofurfuryl aminoester of the formula:

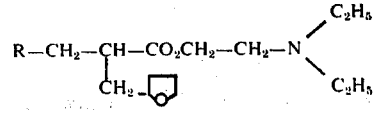

in which R is a member of the group consisting of the 2-naphthyl radical, the 6-alkoxy-2-naphthel radical, and the 5, 6, 7, 8-tetrahydro-1-naphthyl radical.

7. A method in accordance with claim 6, wherein said aminoester is administered at a daily dose between about 150 and 300 mg/kg.

* * * * *